US010750956B2

(12) United States Patent
Zalevsky et al.

(10) Patent No.: US 10,750,956 B2
(45) Date of Patent: Aug. 25, 2020

(54) SYSTEM AND METHOD FOR BLOOD PRESSURE MEASUREMENT

(71) Applicant: ContinUse Biometrics Ltd., Tel Aviv (IL)

(72) Inventors: Zeev Zalevsky, Rosh HaAyin (IL); Yevgeny Beiderman, Tel Aviv (IL); Javier Garcia, Valencia (ES); Mark Golberg, Rehovot (IL); Joaquin Ruiz-Rivas Onses, Madrid (ES)

(73) Assignee: CONTINUSE BIOMETRICS LTD., Tel Aviv (IL)

( * ) Notice: Subject to any disclaimer, the term of this patent is extended or adjusted under 35 U.S.C. 154(b) by 204 days.

(21) Appl. No.: 15/946,223

(22) Filed: Apr. 5, 2018

(65) Prior Publication Data
US 2018/0289270 A1 Oct. 11, 2018

Related U.S. Application Data

(60) Provisional application No. 62/482,354, filed on Apr. 6, 2017.

(51) Int. Cl.
A61B 5/021 (2006.01)
A61B 5/024 (2006.01)
(Continued)

(52) U.S. Cl.
CPC ........ A61B 5/02108 (2013.01); A61B 5/0066 (2013.01); A61B 5/024 (2013.01);
(Continued)

(58) Field of Classification Search
CPC .............. A61B 5/02108; A61B 5/0066; A61B 5/02125; A61B 5/024; G01B 9/02094
See application file for complete search history.

(56) References Cited

U.S. PATENT DOCUMENTS 8,638,991 B2 1/2014 Zalevsky et al.
2006/0036218 A1* 2/2006 Goodson, IV ........ A61M 29/02
604/264

(Continued)

OTHER PUBLICATIONS

Google Scholar Search Results.*

Primary Examiner — Qun Shen
(74) Attorney, Agent, or Firm — Browdy and Neimark, PLLC

(57) ABSTRACT

A system for use in monitoring blood circulation data of a user is disclosed. The system comprising a monitoring unit comprising at least one light source unit configured for providing and directing coherent illumination onto at least one selected inspection region on the user's body, and a collection unit configured for collecting light returning for at least a portion of the inspection region and generating a plurality of image data pieces associated with secondary speckle patterns in the collected light returning from said regions; and a control unit configured and operable for receiving said plurality of image data pieces, determining correlation functions between speckle patterns in consecutive image data pieces, processing said correlation functions for determining data indicative of at least two heart rate data sequence indicative of heart rate of the user, and determining data indicative of circulation pressure of the user in accordance with said data indicative of heart rate of the user measured at said first and second monitoring regions.

11 Claims, 8 Drawing Sheets

(51) Int. Cl.
   *G01B 9/02* (2006.01)
   *A61B 5/00* (2006.01)
   *A61B 5/11* (2006.01)

(52) U.S. Cl.
   CPC ...... *A61B 5/02125* (2013.01); *A61B 5/02444* (2013.01); *G01B 9/02094* (2013.01); *A61B 5/0059* (2013.01); *A61B 5/11* (2013.01); *A61B 5/1102* (2013.01); *G01B 9/02083* (2013.01)

(56) References Cited

U.S. PATENT DOCUMENTS

| | | | |
|---|---|---|---|
| 2006/0149350 A1* | 7/2006 | Patel | A61F 2/954 623/1.11 |
| 2010/0160794 A1* | 6/2010 | Banet | A61B 5/02125 600/485 |
| 2011/0028859 A1* | 2/2011 | Chian | A61B 5/4064 600/554 |
| 2013/0144137 A1 | 6/2013 | Zalevsky et al. | |
| 2013/0158403 A1* | 6/2013 | Gottschalk | A61B 8/065 600/447 |
| 2014/0025037 A1* | 1/2014 | Elkins | A61M 25/0082 604/508 |
| 2014/0148658 A1* | 5/2014 | Zalevsky | A61B 5/0084 600/301 |
| 2014/0266939 A1* | 9/2014 | Baringer | H01Q 21/28 343/729 |
| 2015/0323311 A1* | 11/2015 | Muijs | A61B 5/0059 356/28.5 |
| 2017/0188864 A1* | 7/2017 | Drury | A61B 5/0408 |
| 2017/0209055 A1* | 7/2017 | Pantelopoulos | A61B 5/02108 |

\* cited by examiner

SYSTEM AND METHOD FOR BLOOD PRESSURE MEASUREMENT

TECHNOLOGICAL FIELD

The present invention relates to a system and a method for use in determining biomechanical parameters of a subject. The technique of the invention is relevant especially for measurement of blood pressure of a subject.

BACKGROUND

Increased blood pressure or Hypertension is a highly common and often considered as dangerous condition. According to the American Heart Association one out of every three Americans over the age of 20 have high blood pressure, while many of them might not even know that. Additional blood pressure variations are often associated with various medical issues relating to heart diseases, trauma and injuries, etc. Typically, monitoring of blood pressure is considered to be one of the main parameters to be monitored for every patient. To this end it is a common practice in various medical facilities to measure patients' blood pressure periodically. Such measurement generally utilize application of certain pressure on a patient's arm or other limbs and monitoring its effect on blood flow. Although effective a common, this technique is both time consuming and cause discomfort to the patient during and between measurements.

Various techniques for optically monitoring parameters of an object, especially biological objects, including human body, are known. Some such techniques are based on monitoring temporal correlations between speckle patterns formed by reflection/scattering of coherent light from a monitored sample or tissue. For example:

U.S. Pat. No. 8,638,991 presents a method for imaging an object. The method comprises imaging a coherent speckle pattern propagating from an object, using an imaging system being focused on a plane displaced from the object.

US 2013/0144137 and US 2014/0148658 present a system and method for use in monitoring one or more conditions of a subject's body. The system includes a control unit which includes an input port for receiving image data, a memory utility, and a processor utility. The image data is indicative of data measured by a pixel detector array and is in the form of a sequence of speckle patterns generated by a portion of the subject's body in response to illumination thereof by coherent light according to a certain sampling time pattern. The memory utility stores one or more predetermined models, the model comprising data indicative of a relation between one or more measurable parameters and one or more conditions of the subject's body. The processor utility is configured and operable for processing the image data to determine one or more corresponding body conditions; and generating output data indicative of the corresponding body conditions.

General Description

There is a need in the art for novel techniques enabling monitoring of biological parameters. The present invention provides a technique enabling remote, optically obtained, measurement of circulation pressure data. More specifically, the technique enables detection of blood pressure of a user/patient while eliminating, or at least significantly reducing, a need to apply external pressure of the user or any part of the user's body.

The technique of the invention is based on determining blood pulse-wave velocity by providing heart rate measurements at two spatially separated locations on the user's body. Utilizing the obtained pulse-wave velocity data, e.g. in accordance with pre-provided calibration data, and determining data about blood pressure of the user. Accordingly, the present technique enables determining blood pressure parameters continuously and remotely, while eliminating, or at least significantly reducing, a need to apply physical pressure on the user.

Generally, the technique of the present invention may utilize speckle-based monitoring technique for determining heart rate data of the patient. The heart rate measurements may thus be obtained or provided by collecting a plurality of image data pieces indicative of secondary speckle patterns from at least first and second monitoring regions on the user's body. The collected image data pieces may be processed for determining heart rate data streams as detected in the at least first and second monitoring regions, and the pulse-wave velocity can be determined based on correlation between heart rate data streams.

More specifically, the speckle-based monitoring technique utilizes determining time-varying correlation functions between consecutive speckle patterns for determining data on vibrations of the regions being inspected. Such vibrations, typically filtered to selected frequency range, provide data indicative of heart activity and/or heart rate of the user.

The heart rate data streams from at least the first and second monitoring regions is processed using data about distance between the monitoring regions. The processing generally comprises determining correlation between heart rate measures from the different monitoring regions, also associated as phase variations between the heart rate data streams. The time variations between the different heart rate data streams enable to determine data about pulse wave velocity of blood, which is typically associated with blood pressure. The technique may further utilizes pre-sorted calibration data for determining blood pressure data in accordance with the pulse-wave velocity data.

The at least first and second monitoring regions are generally selected to be along certain path of blood flow in the patient's body. More specifically, the first region may be located on a limb (e.g. arm or leg) at a proximal position (closer to the heart) and the second region may be on the same limb but at a distal position (further from the heart. The regions may be separated by one or more millimeters or more between them, the regions may be separated by a few millimeters to a few centimeters between them. It should be noted that the at least first and second (and generally additional regions if used) may be defined by corresponding illumination spots on body of the patient. Each monitoring region may be associated with at least a portion of an illumination spot, where locations of the illumination spots are determined by directing two or more coherent illumination beams toward the selected monitoring region. Alternatively or additionally, selection of the different monitoring regions may be determined by field of view of corresponding collection units. This enables monitoring data using a large illumination region and collection of speckle patterns data from at least first and second portions of the single inspection region, i.e. proximal and distal portions of the same region.

In some configurations of the invention, the present technique may utilized sequence of image data piece collected from one or more regions of the subject's body. The processing comprises determining two partially overlapping heart rate signals associated with blood flowing through arteries and return flow through the veins. The two partially overlapping signals may be detected from a single monitoring region. The arterial and vein related heart rate data may be processed as heart rate data collected from two different monitoring regions for determining circulation data, e.g. blood pressure, of the subject.

Thus, according to a broad aspect, the present invention provides a system for use in monitoring blood circulation data of a user, the system comprising a monitoring unit comprising at least one light source unit configured for providing and directing coherent illumination onto at least one selected inspection region on the user's body, and a collection unit configured for collecting light returning for at least a portion of the inspection region and generating a plurality of image data pieces associated with secondary speckle patterns in the collected light returning from said regions; and a control unit configured and operable for receiving said plurality of image data pieces, determining correlation functions between speckle patterns in consecutive image data pieces, processing said correlation functions for determining data indicative of at least two heart rate data sequence indicative of heart rate of the user, and determining data indicative of circulation pressure of the user in accordance with said data indicative of heart rate of the user measured at said first and second monitoring regions.

According to some embodiments, the at least two heart rate data sequence may comprise arterial flow pulse beats and vein flow pulse beats collected from a common inspection region.

According to some other embodiments, the collection unit may be configured for collecting at least two sequences of image data pieces associated with corresponding at least two portions of the at least one selected inspection region.

The at least one light source unit may be configured for illuminating two or more illumination spots associated with said at least two portions of the inspection region, thereby forming at least two monitoring positions.

The at least two portions of the inspection region may comprise at least one proximal position and at least one distal position.

The at least two portions of the inspection region may comprise at least one measurement position on chest of the user and at least one measurement position on limb of the user.

According to some embodiments, the at least two portions of the inspection region may comprise at least one proximal measurement position on a limb of the user and at least one distal measurement position on said limb of the user.

According to some embodiments, the control unit may be configured and operable for determining pulse transit time in accordance with time difference between peaks of heart rate data determined from said at least two portions of the inspection region, and for determining blood pressure data in accordance with at least said pulse transit time and heart rate data.

According to one other broad aspect, the present invention provides a system for use in monitoring blood circulation data of a user, the system comprises at least first and second monitoring units and a control unit; the at least first and second monitoring units include corresponding light source units configured for providing and directing coherent illumination onto first and second monitoring regions on a user's body respectively, and detection units configured for collecting light returning from said first and second monitoring regions and generating corresponding pluralities of image data pieces associated with secondary speckle patterns in the collected light; the control unit is configured and operable for receiving said first and second pluralities of image data pieces, determining correlation functions between speckle patterns in consecutive image data pieces, processing said correlation functions for determining data indicative of heart rate of the user measured at said first and second monitoring regions, and determining data indicative of circulation pressure of the user in accordance with said data indicative of heart rate of the user measured at said first and second monitoring regions.

According to some embodiments, the control unit may be configured and operable for determining pulse transit time associated with time difference between heart rate activity data detected at said first and second monitoring regions, and for utilizing said pulse transit time for determining said data indicative of circulation pressure.

According to some embodiments, determining the data indicative of circulation pressure of the user may comprise determining data about pulse wave velocity in accordance with said data indicative of heart rate of the user measured at said first and second monitoring regions and utilizing pre-stored calibration data for determining said circulation pressure of the user.

According to some embodiments, the data about circulation pressure of the user comprises blood pulse pressure data.

According to yet another broad aspect, the present invention provides a system for use in monitoring blood pressure of a subject, the system comprises at least one monitoring unit and a control unit; the monitoring unit comprises light source unit configured for providing and directing coherent illumination onto at least one monitoring region on a subject's body, and at least one detection unit configured for collecting light returning from said first and second monitoring regions and generating corresponding pluralities of image data pieces associated with secondary speckle patterns in the collected light; the control unit is configured and operable for receiving a plurality of image data pieces, determining correlation functions between speckle patterns in consecutive image data pieces, processing said correlation functions for determining data indicative of heart rate of the user measured at said monitoring region, and determining data indicative of circulation pressure of the user in accordance with at least one pulse structure parameters of said heart rate.

According to some embodiments, the pulse structure parameters comprise at least one parameter selected from: width, height, and the time intervals between peaks forming heart pulse beats.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
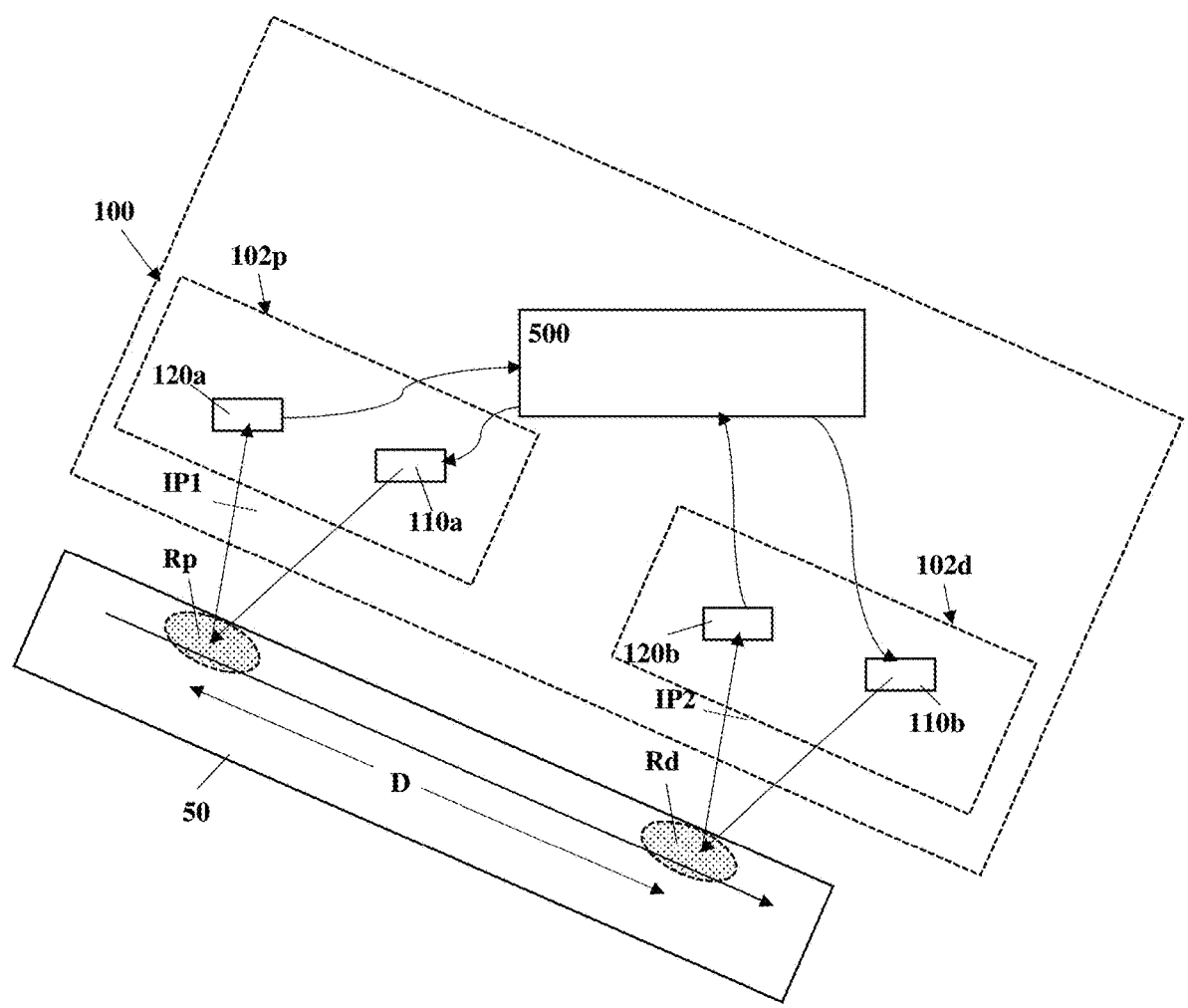
FIG. 1 illustrates a system for monitoring blood pressure of a user according to some embodiments of the present invention.

Reference is made to FIG. 1, illustrating schematically a system 100 configured for providing blood pressure measurement of a user according to some embodiments of the present invention. System 100 includes two or more monitoring units, 102p and 102d as exemplified in the figure, and a control unit 500 configured and operable for operating the two or more monitoring units and for receiving data collected thereby. The system 100 may also include, or be associated with, power source unit, user interface, network connection module and additional other features that are not specifically shown herein. The monitoring units 102p and 102d generally include corresponding light source units 110a and 110b, and detection units 120a and 120b respectively.

Generally, each of the monitoring units 102p and 102d is configured for utilizing speckle-based monitoring of a region of interest. Accordingly, the light source units 110a and 100b are configured for providing coherent optical radiation of one or more predetermined wavelength range, and directing the optical radiation to corresponding monitoring regions Rp and Rd on a portion of the subject's body 50 and spaced between them by a predetermined distance D. The detection units 120a and 120b are configured for obtaining defocused images associated with light components returning from the monitoring regions Rp and Rd and forming corresponding sequences of image data pieces. The so-collected image data pieces include secondary speckle patterns formed by interference of light components scattered from the monitoring regions Rp and Rd, which using the speckle based monitoring technique can be processed for determining various parameters of the monitoring regions includes e.g. heart rate of the patient.

Thus, the first and second monitoring units (102p and 102d) are configured for monitoring data indicative of heart rate of the user at two or more corresponding different locations on the user's body, marked herein as Rp and Rd, having distance D between them. Typically, the different locations may be selected to be relatively close between them, e.g. at a distance of a few millimeters or a few centimeters between them, and along a common body feature or limb. This provide proximal monitoring location Rp and distal monitoring location Rd being substantially in path of blood flow in the user's body.

The first and second monitoring units 102p and 102d are configured for monitoring data associated with heart rate measured at the corresponding monitoring regions Rp and Rd. More specifically, the monitoring units may include corresponding light source units 110a and 110b configured for providing coherent illumination and directing it toward the respective inspection regions Rp and Rd. The detection units 120a and 120b are configured for collecting light returning from the inspection regions Rp and Rd and generate sequences of image data pieces, defocused with respect to the monitoring region Rp and Rd. More specifically, the detection units 120a and 120b may generally include imaging lens arrangement and detector array, where the imaging lens arrangement is positions to provide defocused images, e.g. associated with intermediate planes of light collection IP1 and IP2 respectively, on the detector arrays. The so generated image data pieces include secondary speckle patterns formed by light interference due to scattering/reflecting of light from the inspection regions.

Figure 2:
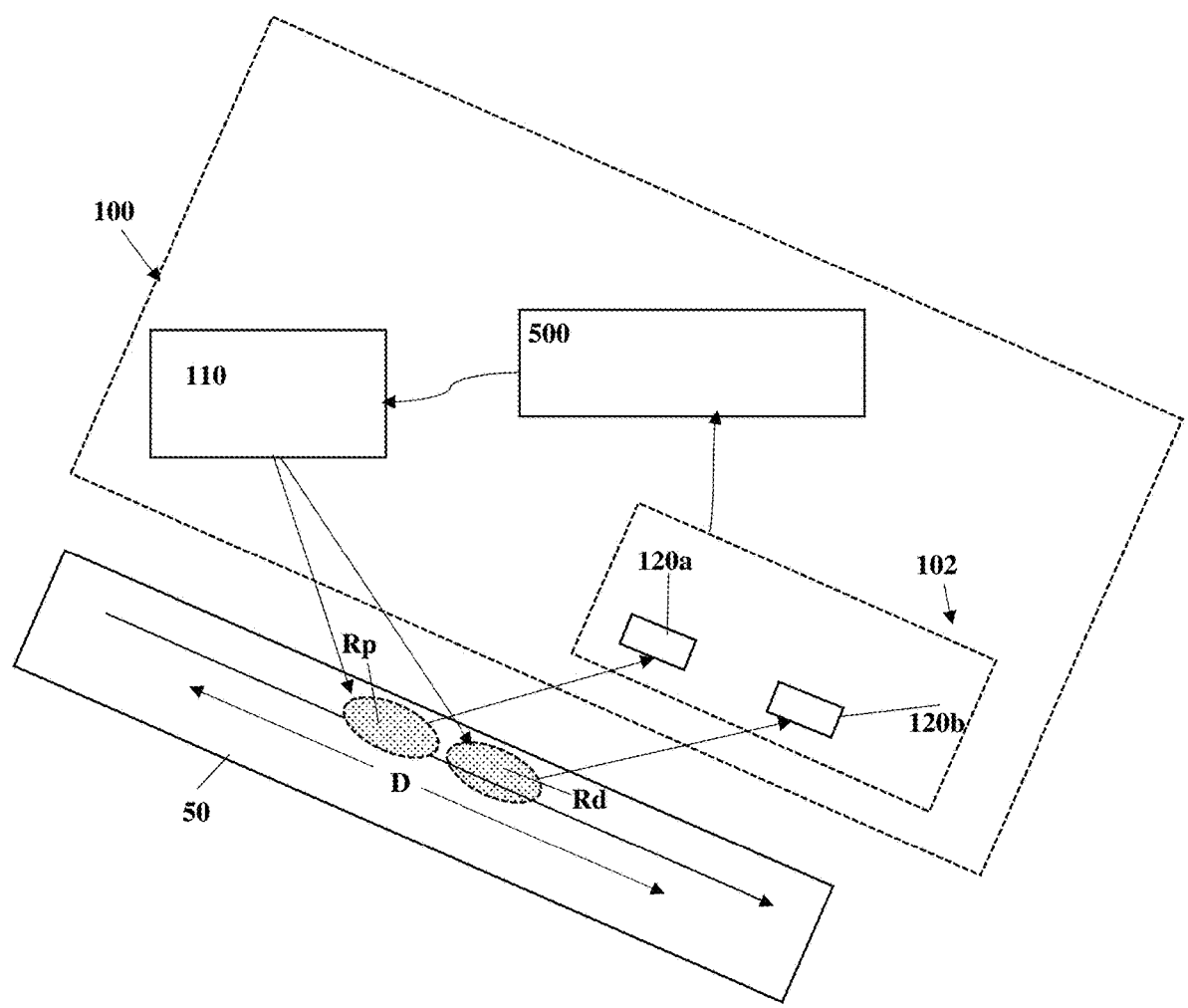
FIG. 2 illustrates an additional configuration of a system for monitoring blood pressure of a user according to some additional embodiments of the invention.

Reference is made to FIG. 2 illustrating another exemplary configuration of system 100. In this example, the system includes an illumination unit 110 configured for directing coherent illumination for illuminating the at lease first and second monitoring regions Rp and Rd on a portion of the subject's body 50 and being separate illumination spots or portions of a common illumination spot. The system also includes image collection unit 102 including at least two detection modules 120a and 120b. Operation and performance of the system and the respective units is generally similar to those described in connection to FIG. 1 other to note that generally, imaging lens arrangements of the detection modules 120a and 120b are configured for collection of light returning from the corresponding monitoring regions Rp and Rd such that each detection module is configured for collecting light from a respective monitoring region. This may be provided, e.g. using field stop apertures in the respective imaging lens arrangement, limiting field of view of the detection units 120a and 120b.

It should further be noted, that the present technique is exemplified herein as utilizing first and second monitoring units for simplicity. Generally, the present technique may utilize one or more monitoring units, e.g. a single monitoring unit, configured for inspection of an inspection region having first and second portions. Accordingly, the so-generated image data is indicative of speckle patterns formed by light returning from at least two portions of the inspection region, enabling the control unit for separately processing data about the different portions to thereby determine heart rate data from at least two different portions of the inspection region. Alternatively, the first and second monitoring regions may be illuminated with light of first and second wavelength ranges. This enables collection of image data including speckle patterns of the first and second monitoring regions with a single detection unit, while the different speckle patterns may be separated based on wavelength for independent processing to determine heart rate data.

Generally, the collection units 102a and 102b exemplified in FIG. 1 or collection unit 102 as exemplified in FIG. 2, is configured for collecting image data sequences indicative of at least the first and second monitoring regions Rp and Rd. The collected image data sequences are transmitted to the control unit 500 for processing and determining blood pressure data.

Utilizing the sequences of so-collected image data pieces, the control unit 500 is configured and operable for determining correlation between consecutive image data pieces and the speckle patterns therein. As previously described, variations on so-collected speckle patterns are indicative of variations in location or orientation of the inspected region. Accordingly, monitoring variations in collected speckle patterns provides data indicative of mechanical vibrations at the inspected region, which may be associated with heart rate pulses forcing blood within the user's arteries.

Figure 3:
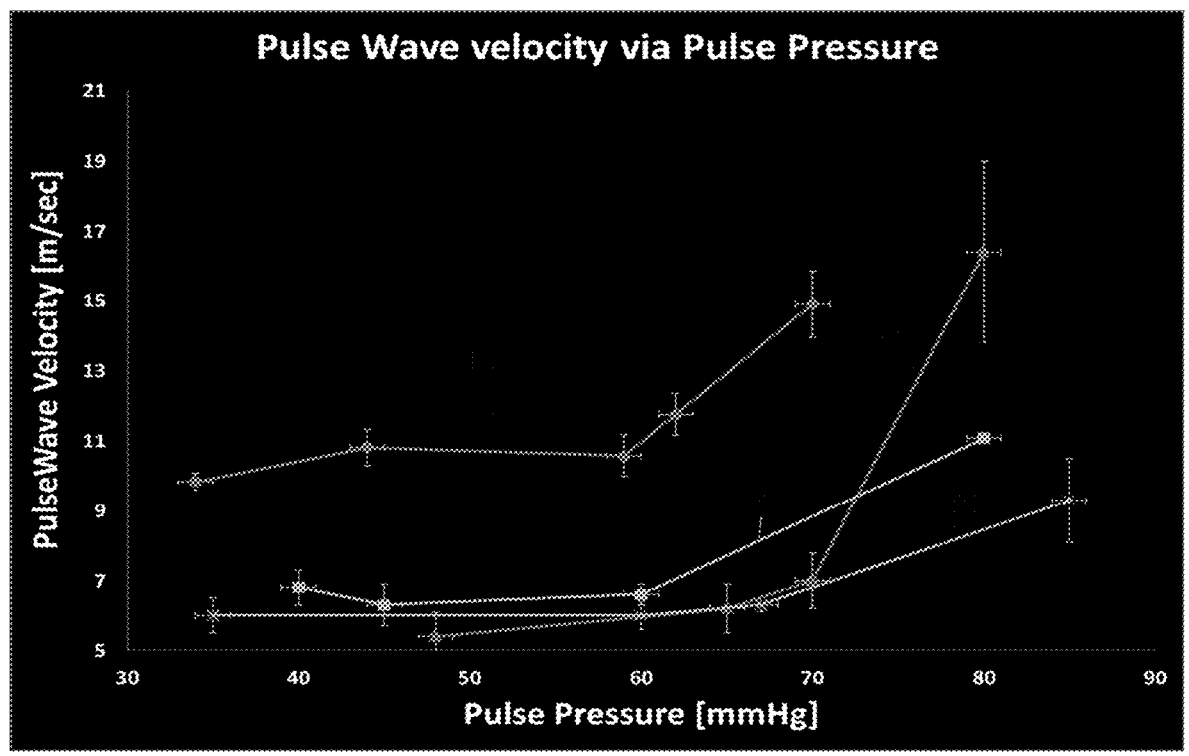
FIG. 3 shows experimental results of blood pressure vs. pulse wave velocity data from four different individuals.

Accordingly, the control unit 500 is configured for receiving sequences of image data pieces associated with secondary speckle patterns collected by the two, or more, detection units 120*a* and 120*b*, and for processing the received image data sequences. The control unit is typically configured for determining correlation between consecutive image data pieces, for determining data about vibrations of each of the inspected regions Rp and Rd. The so-determined vibration data may be filtered for obtaining data associated with heart-rate related vibrations. For Example, the control unit 500 may include a filtering unit configured for filtering vibration data for selecting vibrations having frequencies between 40 bpm and 200 bpm, possibly relating to heart rate activity. Additional filtering of the vibration data may be used, e.g. based on vibration pattern and amplitudes. The filtering of vibration data generally enables the control unit to determine heart rate data at each inspection region Rp and Rd. The control unit 500 is further configured for processing the so-obtained heart rate data in accordance with pre-stored or provided data about the distance D between the monitoring locations Rp and Rd for determining data on pulse wave velocity associated with propagation velocity of the pulses, indicating flow of blood at higher pressure along blood stream of the user. The pulse wave velocity data is indicative of user's circulation pressure variations including blood pressure and/or blood pulse pressure. More specifically, the control unit 500 may generally utilize pre-stored calibration data relating to correlation between pulse wave velocity and circulation pressure of the user. FIG. 3 shows experimentally measured data of pulse wave velocity and corresponding pulse pressure of four different individuals P1-P4. The pulse pressure is generally given as difference between systolic and diastolic pressure measures of the user. As can be seen, FIG. 3 provides experimental evidence for a substantially linear relation between pulse wave velocity, measured by correlation of heart rate signals at selected spatial distance D, and parameters associated with blood pressure of the user.

To this end, the control unit 500 is typically pre-stored with calibration data associated with relation between pulse wave velocity and circulation pressure of the user. The calibration data may be generated by periodically measuring user's circulation pressure utilizing one or more of the conventional techniques, e.g. using a pressure cuff while monitoring blood flow through varying pressure levels, and comparing the measured data with data about pulse wave velocity determined as described above.

Generally, as the blood flows through the arteries, pressure waves propagate at a certain velocity, defined as pulse wave velocity (PWV). The PWV generally depends on various parameters associated with elastic properties of both the arteries and the blood. The PWV can be described by Moens-Korteweg equation as a function of vessel and fluid characteristics:

$$PWV = \frac{L}{PTT} = \sqrt{\frac{E \cdot h}{2 \cdot r \cdot \rho}} \quad \text{(equation 1)}$$

where L is the vessel length, PTT is the Pulse Transit Time (corresponding with the time that a pressure pulse spends in transmitting through that length), $\rho$ is the blood density, r is the inner radius of the vessel, h is the vessel wall thickness and E is the elastic modulus of vascular wall. The elasticity parameter E is typically closely related to BP, and may be described as a function of the blood pressure:

$$E = E_0 e^{6\alpha p} \quad \text{(equation 2)}$$

where $\alpha$ is a constant $E_0$ is the zero-pressure modulus of the vessel wall and p is the blood pressure within the vessel.

In accordance with equation 1 and 2, blood pressure data can be determined from the pulse transit time (PTT). This is assuming that the other parameters are constant or slowly varying. Using equation 1 and 2, provides a logarithmic dependency between blood pressure and PTT as follows:

$$BP = -\frac{2}{\alpha} \cdot \ln(PTT) + \frac{\ln\frac{2r\rho L^2}{hE_0}}{\alpha} \quad \text{(equation 3)}$$

As there are many physical factors that can influence cardiac output and blood pressure. For example blood volume, resistance of the blood vessels and blood thickness. The inventors of the present invention have developed a model enabling to determine accurate blood pressure data. The model is based on the inventors understanding that the blood pressure is the outcome of cardiac output and peripheral resistance. Moreover, variation in blood pressure typically results in compensation activity of the heart (changes in heart rate) and in arterial diameters (as arterial walls contract). These variations are generally a result of nervous system stimulations directed at stabilizing physiological parameters. Accordingly, it can be understood that actual heart rate may be an important contributor to provide correct measurements of blood pressure. Thus, the inventors have used variation model based on equation 3 indicating:

$$BP = \beta_1 \cdot \frac{HR}{PTT} + \beta_2 \cdot PTT \quad \text{(equation 4)}$$

where $\beta_1$ and $\beta_2$ are personal calibration parameters, calculated for each subject, separately for systolic and diastolic values.

Figure 4:
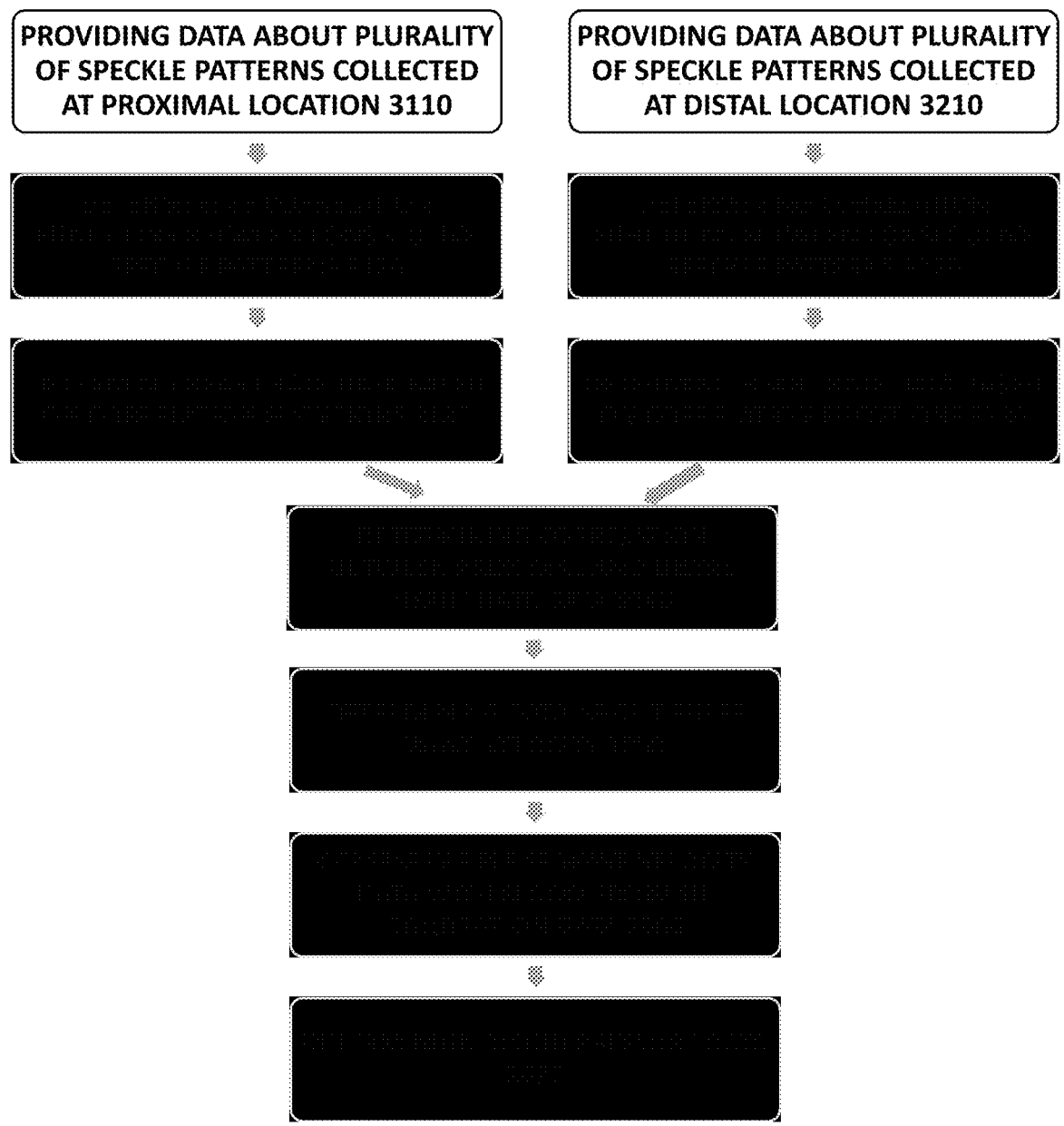
FIG. 4 exemplifies a technique for determining blood pressure data of a user according to some embodiments of the invention.

Reference is made to FIG. 4 illustrating a technique for determining blood pressure data according to some embodiments of the invention. As shown, the technique includes providing data about plurality of speckle patterns collected from at least first proximal monitoring region 3110 and second distal monitoring region 3210; determining corresponding correlation functions for the plurality of speckle patterns 3120 and 3220; and determining data indicative of heart rate measured in the proximal and distal monitoring regions 3130 and 3230. Utilizing the so-provided heart rate data for determining correlation between proximal and distal measurements 3040, and determining pulse wave velocity based on this correlation 3050. Providing pre-stored calibration data indicative of circulation pressure (blood pressure and/or blood pulse pressure) and pulse wave velocity of the user and comparing the pre-stored calibration data with the determined pulse wave velocity data 3060 for determining circulation pressure data of the user 3070.

Typically, the control unit 500 illustrated in FIG. 1 above may include a processing utility including one or more software/hardware modules configured for performing the above describe actions, and a memory/storage utility configured for storing the pre-stored/pre-provided calibration data about circulation pressure relation with pulse wave velocity of the user. Generally, the calibration data may be updated from time to time by providing additional independent blood pressure measurements while monitoring pulse wave velocity data as described above.

The inventors have experimentally tested the present technique for determining blood pressure data pf patients. To this end, subjects were optically monitored from a distance of one meter at two selected sites for determining an estimation for PTT. For convenience the monitoring was performed at one chest position and one wrist position, providing proximal position (chest) and distal position (wrist) that generally form line of blood flow from the heart. Additional monitoring position may be used where both monitoring regions are along an arm or leg of the subject.

The monitoring utilized Biosensors including USB 3 Camera (Basler, acA800-510 um), 780 nm laser diode, objective lens (f35 mm) and an electrical relay for control over the camera on/off state. All the recorded data was post processed in accordance with the above described technique.

For determining pulse transit time, heart rate signals were detected in both the monitoring positions. The pulse signals are generally of different shapes as the measured signals are obtained via vibrations of the skin. The pulse transit time is determined by correlating the heart rate signals and determining time difference between appearances of the pulse peaks at the two positions. The experimental tests included sample size of 11 healthy adult participants of age 18 and up with no cardiac or pulmonary history nor recent illness. Table 1 summarize the participating subjects.

TABLE 1

Subject personal data

| # | Gender | Age (years) | Weight (kg) | Height (cm) | BMI (kg/m$^2$) | Arm length (cm) | Rest Sys BP (mmHg) | Rest Dia BP (mmHg) |
|---|---|---|---|---|---|---|---|---|
| 1 | M | 38 | 66 | 170 | 22.84 | 31 | 115 | 79 |
| 2 | F | 28 | 50 | 176 | 16.14 | 24 | 90 | 72 |
| 3 | M | 33 | 89 | 178 | 28.09 | 30 | 120 | 77 |
| 4 | F | 33 | 58 | 165 | 21.30 | 25 | 117 | 85 |
| 5 | M | 45 | 60 | 183 | 17.92 | 25 | 103 | 63 |
| 6 | F | 53 | 60 | 174 | 19.82 | 24 | 95 | 64 |
| 7 | M | 34 | 85 | 175 | 27.76 | 31 | 123 | 74 |
| 8 | M | 41 | 102 | 176 | 32.93 | 35 | 121 | 86 |
| 9 | M | 25 | 88 | 179 | 27.46 | 32 | 128 | 93 |
| 10 | M | 27 | 72 | 175 | 23.51 | 30 | 114 | 70 |
| 11 | F | 27 | 57 | 156 | 23.42 | 25 | 100 | 75 |

The test subjects were asked to sit for a resting period of 5 minutes, to reach a physiological steady-state. Subsequently, 3 consecutive BP measurements were performed using conventional blood pressure technique (Omron M6 digital blood pressure device) to verify steady-state BP. If the differences between each of the consecutive systolic and diastolic BP reads exceeded 5 mmHg, the subject was asked to remain seated for an additional 1 minute and a 4th measurement was performed. This step was repeated until the differences between consecutive reads were less than 5 mmHg Once this criterion was fulfilled, a SOMNOtouch™ cNIBP reference blood pressure measurement device was calibrated according to the last read given by the Omron M6 device, and the subject was monitored using the present system for determining blood pressure data. The subject was asked to breath normally during the session. Following this calibration step, the subject was asked to leave the test area, and return after 1 hour, for a validation procedure including 5 minutes sitting and 3 comparative tests using the present technique and reference measurements. It should be noted that the tests were conducted while subjects wearing their personal clothing and when at least the chest measurement position is over the subjects' clothes.

Figure 5:
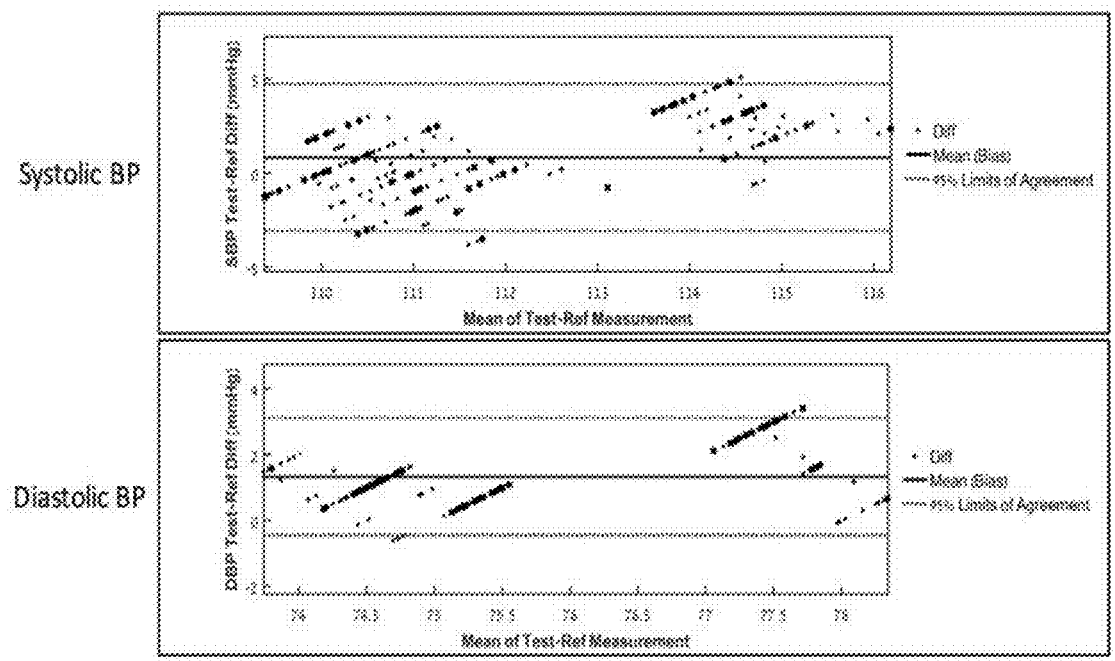
FIG. 5 shows Bland-Altman graphs of difference between blood pressure values determined by the present technique and reference blood pressure values with respect to mean of the determined blood pressure values.

Reference is made to FIG. 5 showing Bland-Altman plots for both systolic (top graph) and diastolic (bottom graph) blood pressure measurements. The graphs show difference between blood pressure data determined by the present technique and using the reference measurements vs. mean values of the two techniques. As shown, the present technique provides above 95% agreement with the conventional blood pressure measuring techniques, while enabling non-contact measurements that does not apply discomfort to the patients.

Figure 6A:
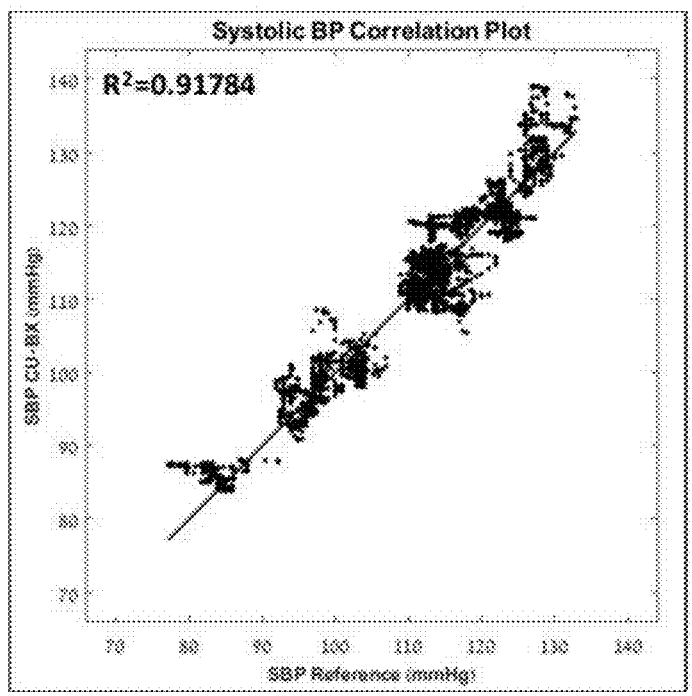
FIGS. 6A and 6B show correlation between systolic (FIG. 6A) and diastolic (FIG. 6B) pressure values determined according to the present technique and reference blood pressure data measured using conventional techniques.
Figure 6B:
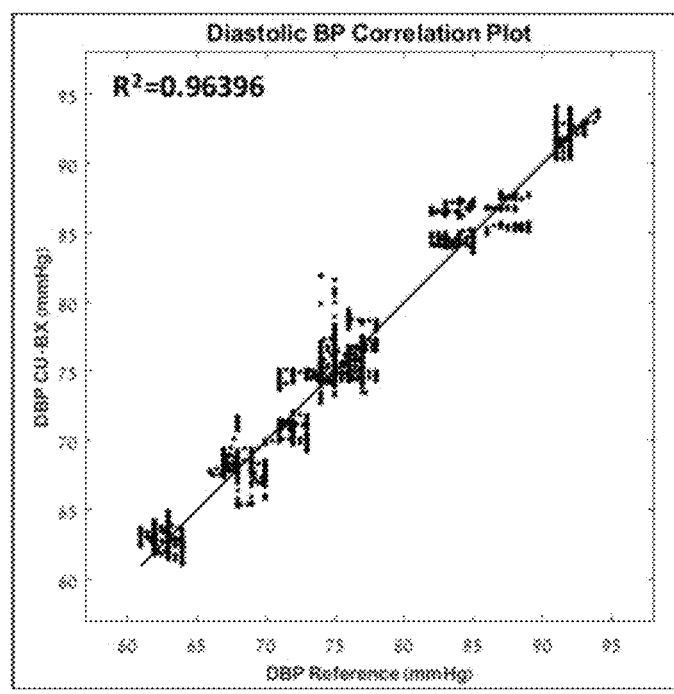

Correlations of both systolic and diastolic blood pressure measurements between the present technique and the reference measurements are shown in FIGS. 6A and 6B. FIG. 6A shows the systolic blood pressure values measured using the present techniques (SBP CU-BX) compared to the systolic reference blood pressure measurements (SBP Reference); FIG. 6B shows similar results (DBP CU-BX vs. DBP Reference) for the diastolic blood pressure values. $R^2$ values were calculated based on a 0-intercepted regression line, with a slope of 1, to evaluate data dispersion relative to a theoretical fully correlated model.

Figure 7:
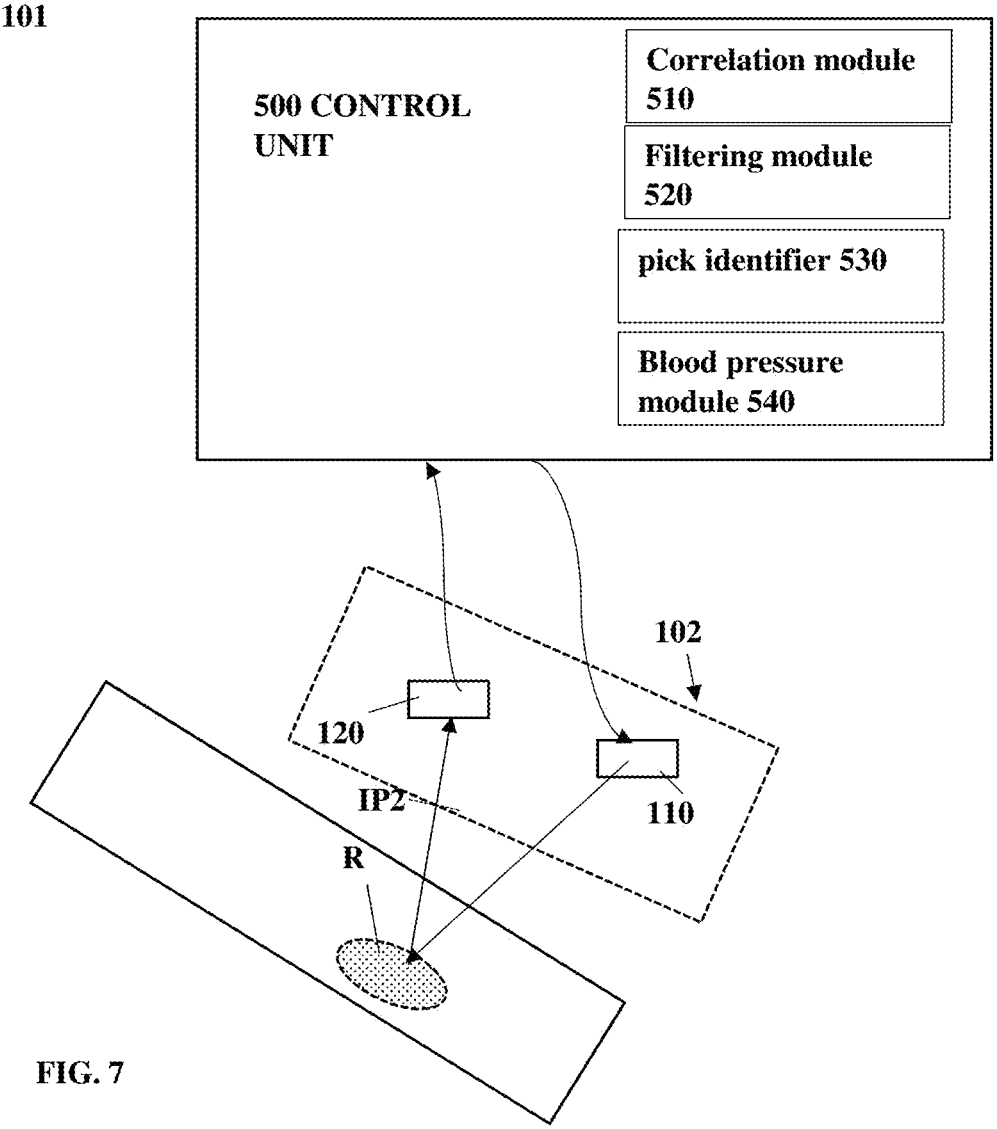
FIG. 7 illustrates a system for use in monitoring circulation parameters according to some other embodiments of the invention.

Based on some further configurations, the system may utilize heart rate data collected from one or more regions on the patient's body for determining data about blood pressure. Reference is made to FIG. 7 illustrating a system 101 for determining blood pressure data of a user. The system 101 includes a collection unit 102 including at least one light source unit 110 and detection unit 120 configured as described above. The collection unit is configured for collecting one or more sequences of image data pieces associated with speckle patterns as described above, and to provide the collected sequence of image data piece to a control unit 500 for processing and determining data about blood pressure of the user.

The control unit 500 is configured for receiving input data in the form of a sequence of image data pieces, each including at least one speckle pattern. Determine correlations between speckle patterns in consecutively collected image data piece for determining at least one time-correlation function indicative of vibrations of the inspection region. And filtering the time-correlation pattern for determining heart rate data. Generally, the control unit may be configured as a computer system including one or more processors, storage utility and input/output ports. The one or more processors are configured for executing operational instructions and may be associated with one or more hardware or software modules such as correlation module 510 configured for determining spatial correlations between the speckle patterns and determining time-correlation function indicative of vibrations at the inspection region; filtering module 520 configured for receiving the time correlation function data and processing it for filtering out noise and determining data indicative of heart rate activity.

The present technique further utilizes the inventors' understanding that vibrational manifestation of the heart activity as measured from different location on the body may provide additional information on the circulation of the patient. To this end, the control unit further includes peaks identifier 530 configured for processing the data about heart rate activity and deterring temporal location and relation of elements of different heart rate pulses. The temporal and structural data about heart rate pulses is further processed by the blood pressure module 540 in accordance with pre-stored data base and computer learning techniques for determining data about blood pressure of the patient.

In some other configurations, the control unit 500 is configured for determining heart rate data associated with blood flow through arteries and veins as two separated heart rate signals, collected from a common monitoring unit. This is provided by identifying repeating pulse beat signals having different amplitude and intensity. The arterial pulse signals are substantially stronger with respect to vein pulse signals. Accordingly, the peak identifier 530 may be configured for identifying pulse beats associated with arterial flow and pulse beats associated with vein blood flow. Data on the different beat sequences is transferred to the blood pressure module 540 for processing and determining blood pressure data in accordance with pulse transit time as described above.

Figure 8:
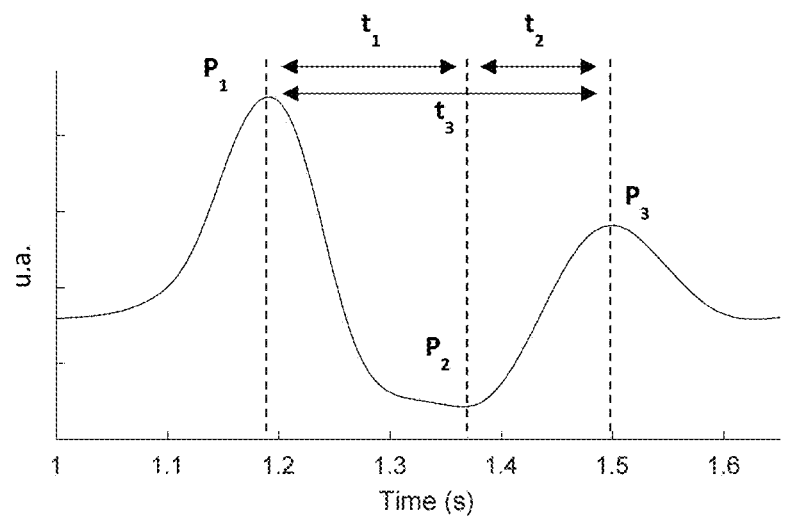
FIG. 8 shows pulse beat structure as used according to some embodiments of the present technique for determining circulation data.

An example of pulse as detected by the present technique, utilising pulse beat structure, is illustrated in FIG. 8. As shown, the vibration pulse typically includes three major peaks (positive and negative peaks) marked as P1, P2 and P3. The peaks are temporally separated between them by time periods t1 and t2 and the total length of the pulse is given by t3 (typically t3=t1+t2). The blood pressure module 540 is configured for processing the filtered time-correlation functions for determining this internal structure of the heart rate data and utilize signal parameters such as width, height, of each one of the peaks, and the time intervals between them, the ratio and frequency band of these parameters. And determining blood pressure data in accordance with pre-stored models and machine learning techniques.

Figure 9:
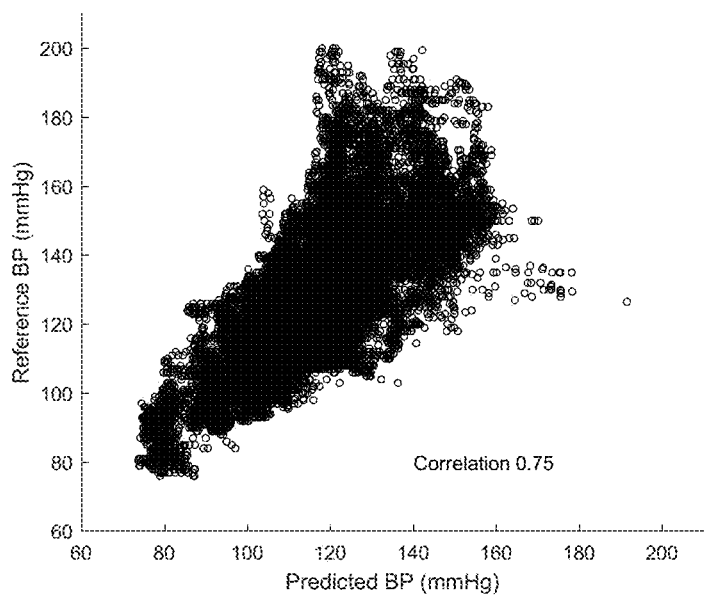
FIG. 9 shows experimental comparison of the present technique for monitoring blood pressure as compared to conventional cuff measuring technique.

Reference is made to FIG. 9 showing experimental results conducted on a group of 48 subjects for determining their blood pressure data using the present technique. The subjects were instructed to exercise for selected periods and then were instructed to sit for determining their blood pressure. Given the exercise, it is expected that the blood pressure will be slightly higher than the normal state of the subjects. The subjects were measured using the present technique from one body location for determining blood pressure based on pulse shape parameters and the determined results were compared to conventional blood pressure measurement using a cuff device. The process was repeated twice for increasing data and accuracy. FIG. 9 shows results in the form of a graph illustrating relation between the blood pressure data as determined by the present technique and that measured by the cuff device. As shown the results show 0.75 correlation parameter, providing good approximation.

Accordingly, the above described technique provides a technique and a system for determining and monitoring circulation pressure data of a user while in a substantially contact-free measurement technique. The technique of the invention enables continuous monitoring while eliminates or at least significantly reduces the need to apply physical pressure on any body part of the user and accordingly provides seamless measurement that does not affect the user's comfort.

The invention claimed is:

1. A system for use in monitoring blood circulation data of a user, the system comprising
a monitoring unit comprising at least one light source unit configured for providing and directing coherent illumination onto at least one selected inspection region on the user's body, and a collection unit configured for collecting light returning for at least first and second portions of the at least one selected inspection region and generating corresponding first and second pluralities of image data pieces associated with secondary speckle patterns in the collected light returning from said at least first and second portions of the at least one selected inspection regions; and
a control unit configured and operable for receiving said first and second pluralities image data pieces, determining first and second correlation functions between speckle patterns in consecutive image data pieces, processing said first and second correlation functions for determining data indicative of at least two heart rate data sequences indicative of heart rate of the user, and determining data indicative of circulation pressure of the user in accordance with said data indicative of at least two heart rate sequences of the user measured at said first and second portions of the at least one selected inspection region;
wherein said at least two portions of the inspection region comprising at least one proximal position and at least one distal position;
wherein said at least one proximal position and at least one distal position are separated by up to 3 centimeters; and
wherein said at least one proximal position and at least one distal position are along a common body feature.

2. The system of claim 1, wherein said at least two heart rate data sequence comprise arterial flow pulse beats and vein flow pulse beats collected from a common inspection region.

3. The system of claim 1, wherein said at least one light source unit is configured and operable to illuminate two or more illumination spots associated with said at least two portions of the inspection region, thereby forming at least two monitoring positions.

4. The system of claim 1, wherein said at least two portions of the inspection region comprise at least one measurement position on chest of the user and at least one measurement position on limb of the user.

5. The system of claim 1, wherein said at least two portions of the inspection region comprise at least one proximal measurement position on a limb of the user and at least one distal measurement position on said limb of the user.

6. The system of claim 1, wherein said control unit is configured and operable for determining pulse transit time in accordance with time difference between peaks of heart rate data determined from said at least two portions of the inspection region, and for determining blood pressure data in accordance with at least said pulse transit time and heart rate data.

7. A system for use in monitoring blood circulation data of a user, the system comprises: at least first and second monitoring units, and a control unit;
- wherein the at least first and second monitoring units include corresponding light source units configured for providing and directing coherent illumination onto first and second monitoring regions on a user's body respectively, and detection units configured for collecting light returning from said first and second monitoring regions and generating corresponding pluralities of image data pieces associated with secondary speckle patterns in the collected light;
- wherein the control unit is configured and operable for receiving said first and second pluralities of image data pieces, determining correlation functions between speckle patterns in consecutive image data pieces, processing said correlation functions for determining data indicative of heart rate of the user measured at said first and second monitoring regions, and determining data indicative of circulation pressure of the user in accordance with said data indicative of heart rate of the user measured at said first and second monitoring regions;
- wherein said first and second monitoring regions on the user's body comprise first proximal region and second distal region;
- wherein said at least one proximal position and at least one distal position are separated by up to 3 centimeters; and
- wherein said at least one proximal position and at least one distal position are along a common body feature.

8. The system of claim 7, wherein said control unit is configured and operable for determining pulse transit time associated with time difference between heart rate activity data detected at said first and second monitoring regions, and for utilizing said pulse transit time for determining said data indicative of circulation pressure.

9. The system of claim 7, wherein said determining data indicative of circulation pressure of the user comprises determining data about pulse wave velocity in accordance with said data indicative of heart rate of the user measured at said first and second monitoring regions and utilizing pre-stored calibration data for determining said circulation pressure of the user.

10. The system of claim 7, wherein said data about circulation pressure of the user comprises blood pulse pressure data.

11. The system of claim 7, wherein said data about circulation pressure of the user comprises blood pressure data.

* * * * *